(12) United States Patent
Chen

(10) Patent No.: US 11,315,349 B2
(45) Date of Patent: Apr. 26, 2022

(54) METHOD, APPARATUS AND DEVICE FOR IDENTIFYING PASSENGER STATE IN UNMANNED VEHICLE, AND STORAGE MEDIUM

(71) Applicant: Apollo Intelligent Driving Technology (Beijing) Co., Ltd., Beijing (CN)

(72) Inventor: Youhan Chen, Haidian District Beijing (CN)

(73) Assignee: Apollo Intelligent Driving Technology (Beijing) Co., Ltd., Haidian District (CN)

( * ) Notice: Subject to any disclaimer, the term of this patent is extended or adjusted under 35 U.S.C. 154(b) by 52 days.

(21) Appl. No.: 16/516,137

(22) Filed: Jul. 18, 2019

(65) Prior Publication Data

US 2020/0082187 A1 Mar. 12, 2020

(30) Foreign Application Priority Data

Sep. 10, 2018 (CN) .......................... 201811050981.5

(51) Int. Cl.
*G06K 9/00* (2006.01)
*G06V 20/59* (2022.01)
(Continued)

(52) U.S. Cl.
CPC ............ *G06V 20/59* (2022.01); *A61B 5/0077* (2013.01); *A61B 5/0205* (2013.01);
(Continued)

(58) Field of Classification Search
CPC ........... G06K 9/00302; G06K 9/00355; G06K 9/00832; G06K 9/00845; G06K 9/629;
(Continued)

(56) References Cited

U.S. PATENT DOCUMENTS 7,110,570 B1 * 9/2006 Berenz .................... B60R 25/25
382/104
10,759,424 B2 * 9/2020 Misu ..................... B60W 30/14
(Continued)

FOREIGN PATENT DOCUMENTS

CN 104331953 A 2/2015
CN 105608884 A 5/2016
(Continued)

OTHER PUBLICATIONS

Research and Implementation of Health Monitoring System for Vehicle Driver dated May 20, 2012.
(Continued)

*Primary Examiner* — Avinash Yentrapati
(74) *Attorney, Agent, or Firm* — Tucker Ellis LLP; Tanya Gaylord

(57) ABSTRACT

Embodiments of the present application provide a method, an apparatus, and a device for identifying a passenger state in an unmanned vehicle, and a storage medium. The method comprises: obtaining monitoring data of different dimensions in a process where the passenger takes the unmanned vehicle; performing feature extraction on the monitoring data of the different dimensions and forming feature data of different dimensions; and identifying the passenger state according to the feature data of the different dimensions. By obtaining the monitoring data of various dimensions in the process where the passenger takes the unmanned vehicle to identify the passenger state, it is possible to omnidirectionally monitor the personal is safety and property safety of the passengers, and effectively protect the passenger taking the unmanned vehicle.

12 Claims, 5 Drawing Sheets

(51) Int. Cl.
  *G07C 5/08*  (2006.01)
  *G10L 25/51*  (2013.01)
  *G10L 25/03*  (2013.01)
  *A61B 5/0205*  (2006.01)
  *A61B 5/11*  (2006.01)
  *A61B 5/00*  (2006.01)
  *G06K 9/62*  (2022.01)
  *G06V 40/20*  (2022.01)
  *G06V 40/16*  (2022.01)

(52) U.S. Cl.
  CPC .......... *A61B 5/1128* (2013.01); *A61B 5/6893* (2013.01); *G06K 9/629* (2013.01); *G06V 40/174* (2022.01); *G06V 40/28* (2022.01); *G07C 5/0866* (2013.01); *G10L 25/03* (2013.01); *G10L 25/51* (2013.01)

(58) Field of Classification Search
  CPC .. G06K 9/6293; A61B 5/0077; A61B 5/0205; A61B 5/1128; A61B 5/6893; G07C 5/0866; G10L 25/03; G10L 25/51
  See application file for complete search history.

(56) References Cited

U.S. PATENT DOCUMENTS

| | | | | |
|---|---|---|---|---|
| 2003/0125854 A1* | 7/2003 | Kawasaki | ............ | G07C 5/0891 701/431 |
| 2014/0309864 A1* | 10/2014 | Ricci | .................... | B60N 2/0244 701/36 |
| 2015/0379362 A1* | 12/2015 | Calmes | ..................... | G06T 7/20 348/136 |
| 2016/0001781 A1* | 1/2016 | Fung | ....................... | B60K 28/02 701/36 |
| 2016/0046298 A1* | 2/2016 | DeRuyck | ............. | B60W 50/14 340/576 |
| 2016/0379466 A1 | 12/2016 | Payant et al. | | |
| 2017/0357866 A1 | 12/2017 | Welland et al. | | |

FOREIGN PATENT DOCUMENTS

| CN | 106297189 A | 1/2017 |
|---|---|---|
| CN | 107212861 A | 9/2017 |
| CN | 107212897 A | 9/2017 |
| CN | 107215307 A | 9/2017 |
| CN | 107571735 A | 1/2018 |
| CN | 107634991 A | 1/2018 |
| CN | 107703931 A | 2/2018 |
| CN | 107791840 A | 3/2018 |
| CN | 107791974 A | 3/2018 |
| CN | 107958269 A | 4/2018 |
| CN | 108001158 A | 5/2018 |
| CN | 108146360 A | 6/2018 |
| CN | 108492053 A | 9/2018 |
| JP | H04-305759 A | 10/1992 |
| JP | H06227360 A | 8/1994 |
| JP | 2010079472 A | 4/2010 |
| JP | 2015532743 A | 11/2015 |
| JP | 2017024653 A | 2/2017 |
| WO | 00/54008 A1 | 9/2000 |
| WO | 2014015990 A1 | 1/2014 |
| WO | 2018047392 A1 | 3/2018 |

OTHER PUBLICATIONS

Third Office Action for Chinese Application 201811050981.5 dated Jun. 9, 2021.
Decision of Rejection for Japanese Application 2019-130227 dated Jul. 20, 2021.
European Search Report regarding Application No. 19187077.3-1207 dated Jan. 29, 2020; 9 pages.
Mangai et al.; (2010) A Survey Decision Fusion and Feature Fusion Strategies for Pattern Classification; IETE Technical Review; 16 pages.
CNBLUSP201904449; The first office action of parallel JP application; 5 pages.
CNBLUSP201904449—The Second Office Action of the parallel JP application dated Feb. 16, 2021; 6 pages.
The First Office Action of the Priority Application No. 201811050981.5 dated May 7, 2020; 8 pages.
Dingus, et al. "Driver Crash Risk Factors and Prevalence Evaluation using Naturalistic Driving Data," PNAS Early Edition, Virginia Tech Transportation Institute, Virginia Polytechnic Institute and State University, Blacksburg, VA and Department of Statistics, Virginia Polytechnic Institute and State University, Blacksburg VA, Jan. 26, 2016.
"Research of Urban Road Crash Analysis based on Multivariate Statistical Techniques," May 2010.
Zhao Youjin, "Research on Evaluation Model of Health Statement Based on Deep Learning from Multiple Physiological Big Data," College of Automation of Chongqing University, Chongqing, China, Apr. 2017.
Chinese Notice of Allowance dated Jan. 13, 2022 for Application Serial No. 201811050987.5.

* cited by examiner

METHOD, APPARATUS AND DEVICE FOR IDENTIFYING PASSENGER STATE IN UNMANNED VEHICLE, AND STORAGE MEDIUM

CROSS-REFERENCE TO RELATED APPLICATION

This application claims priority to Chinese Patent Application No. 201811050981.5, filed on Sep. 10, 2018 and entitled "Method, Apparatus and Device for Identifying Passenger State in Unmanned Vehicle, and Storage Medium," which is hereby incorporated by reference in its entirety.

TECHNICAL FIELD

Embodiments of the present application relate to the field of unmanned driving technology, and in particular, to a method, an apparatus, and a device for identifying a passenger state in an unmanned vehicle and a storage medium.

BACKGROUND

With the developments of the Internet and the economy, in order to meet people's travel demand, unmanned driving technology has achieved rapid development. Unmanned driving car is a type of smart car, also known as wheeled mobile robot, which relies mainly on a computer-based intelligent pilot in the car to achieve the goal of unmanned driving.

There is no driver in the unmanned vehicle. When the passenger is traveling in an unmanned vehicle, it is essential to monitor the passenger state omnidirectionally to ensure the personal safety and property safety of the passenger.

In the prior art, the passenger's body is monitored mainly by means of a device carried by the passenger, such as a smart wristband. And when a threat is posed to the passenger's personal safety, the situation is reported by a smart wristband or a mobile phone. However, this method cannot omnidirectionally monitor the personal safety and property safety of passengers, and cannot effectively protect the passengers taking unmanned vehicles.

SUMMARY

Embodiments of the present application provide a method, an apparatus, and a device for identifying a passenger state in an unmanned vehicle, and a storage medium, which solve the problem that the passenger's personal safety and property safety cannot be omnidirectionally monitored and the passenger taking the unmanned vehicle cannot be effectively protected in the method for identifying the passenger state in the prior art.

A first aspect of the embodiments of the present application provides a method for identifying a passenger state in an unmanned vehicle, including: obtaining monitoring data of different dimensions in a process where a passenger takes the unmanned vehicle; performing feature extraction on the monitoring data of different dimensions and forming feature data of different dimensions; identifying the passenger state according to the feature data of different dimensions.

A second aspect of the embodiments of the present application provides an apparatus for identifying a passenger state in an unmanned vehicle, including: a data obtaining module, configured to obtain monitoring data of different dimensions in a process where a passenger takes the unmanned vehicle; and a feature extraction module, configured to perform feature extraction on the monitoring data of different dimensions, and form feature data of different dimensions; and a state identification module, configured to identify the passenger state according to the feature data of different dimensions.

A third aspect of the embodiments of the present application provides a terminal device, including: one or more processors; a storage apparatus, configured to store one or more programs; and a data collecting apparatus, configured to collect monitoring data of different dimensions; the one or more programs, when executed by the one or more processors, cause the one or more processors to implement the method of the first aspect described above.

A fourth aspect of the embodiments of the present application provides a computer readable storage medium having stored thereon a computer program; the program is executed by the processor to implement the method of the first aspect described above.

Based on the above aspects, the embodiments of the present application obtain monitoring data of different dimensions in a process where a passenger takes an unmanned vehicle, performs feature extraction on the monitoring data of different dimensions and forms feature data of different dimensions, identifies the passenger state according to the feature data of different dimensions. By obtaining the monitoring data of various dimensions in the process where the passenger takes the unmanned vehicle to identify the passenger state, it is possible to omnidirectionally monitor the personal safety and property safety of the passengers, and effectively protect the passenger taking the unmanned vehicle.

It should be understood that the content described in the above summary section of the application is not intended to limit the key or important features of the embodiment of the present application, and is not intended to limit the scope of the present application. Other features of the present application will be readily understood with reference to the following description.

DETAILED DESCRIPTION OF THE EMBODIMENTS

Figure 1:
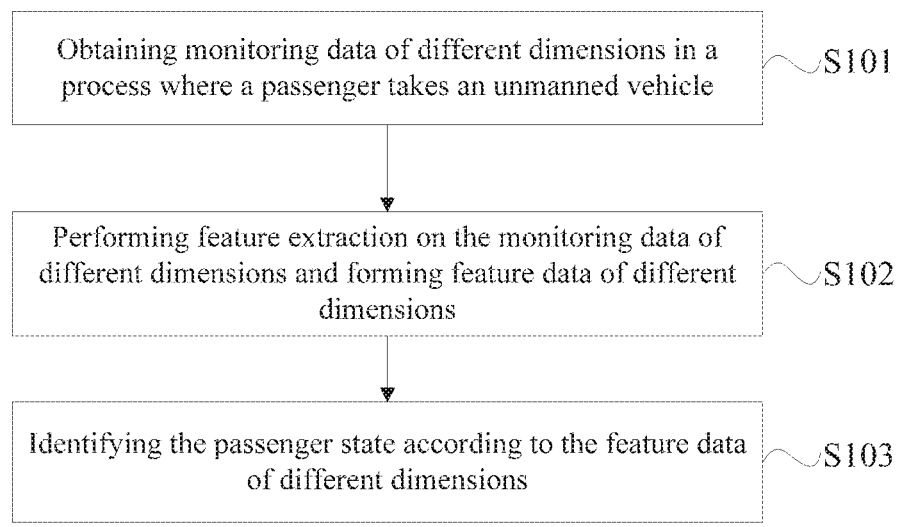
FIG. 1 is a flowchart of a method for identifying a passenger state in an unmanned vehicle according to Embodiment 1 of the present application.

Embodiments of the present application will be described in more detail below with reference to the accompanying drawings. Although some embodiments of the present application are shown in the drawings, it should be understood that the present application may be embodied in a variety of forms and should not be construed as limited to the embodiments set forth herein, on the contrary, these embodiments are provided to make the present disclosure understood more thoroughly and completely. It should be understood that the drawings and the embodiments of the present application are for the purpose of illustration only and not for limiting the protection scope of the present application.

The terms "first", "second", "third", "fourth", etc. (if present) in the description and claims of the embodiments of the present application and the above figures are used to distinguish similar objects, and not necessarily to describe a particular sequence or sequential order. It should be understood that the data used in this way may be interchanged where appropriate, such that the embodiments of the present application described herein can be implemented, for example, in a sequence other than those illustrated or described herein. In addition, the terms "comprise" and "having" and any variations of them are intended to cover a non-exclusive inclusion, for example, processes, methods, systems, products, or devices that include series of steps or units are not necessarily limited to those explicitly listed steps or units, but may include other steps or units that are not explicitly listed or inherent to such processes, methods, products or devices.

In order to clearly understand the technical solution of the present application, the terms involved in the present application are explained below:

Unmanned driving car: an unmanned driving car is a smart car that senses the road environment through the in-vehicle sensing system, automatically plans the driving route and controls the vehicle to reach the predetermined target. It uses the on-board sensor to sense the surrounding environment of the vehicle, and controls the steering and speed of the vehicle according to the road, vehicle position and obstacle information obtained by sensing, so that the vehicle can travel safely and reliably on the road. It integrates many technologies such as automatic control, architecture, artificial intelligence and visual computing, is a product of high development of computer science, pattern identification and intelligent control technology, and is also an important symbol of the scientific research strength and industrial level of a country, with broad application prospects in the national defense area and national economy area. In embodiments of the present application, the unmanned driving car is referred to as an unmanned vehicle.

Embodiments of the present application will be specifically described below with reference to the drawings.

Embodiment 1

FIG. 1 is a flowchart of a method for identifying a passenger state in an unmanned vehicle according to Embodiment 1 of the present application. As shown in FIG. 1, an executive body of the embodiment of the present application is an identification apparatus for identifying a passenger state in an unmanned vehicle. The identification apparatus for identifying the passenger state in the unmanned vehicle can be integrated in a terminal device. The terminal device is an in-vehicle terminal device in the unmanned vehicle. The method for identifying the passenger state in the unmanned vehicle provided in this embodiment includes the following steps.

Step 101: obtaining monitoring data of different dimensions in a process where a passenger takes an unmanned vehicle.

Specifically, in this embodiment, the identification apparatus for identifying the passenger state in the unmanned vehicle may be enabled to communicate with different types of sensors in the unmanned vehicle, and obtain monitoring data of different dimensions in the process where the passenger takes the unmanned vehicle; alternatively, different sensors in the unmanned vehicle may directly collect monitoring data of corresponding dimensions in the process where the passenger takes the unmanned vehicle.

In this case, different types of sensors in the unmanned vehicle may include: an internal camera, a microphone, a vital sign sensor, a collision sensor, and the like. Correspondingly, the monitoring data of different dimensions may include: expression monitoring data, limb movement monitoring data, sound monitoring data, vital sign monitoring data, collision data of colliding a vehicle body or a seat, and the like.

Step 102: performing feature extraction on the monitoring data of different dimensions and forming feature data of different dimensions.

Further, in this embodiment, the monitoring data of each dimension may be extracted by using a corresponding feature extraction algorithm to form feature data of each dimension.

Performing feature extraction on the monitoring data of different dimensions and forming feature data of different dimensions are illustrated as follows: for the expression monitoring data, expression feature extraction algorithm is used for the feature extraction, where the expression feature extraction algorithm can be a PCA feature extraction algorithm, an ICA feature extraction algorithm, etc. For the sound monitoring data, a sound feature extraction algorithm is used for the feature extraction, where the sound feature extraction algorithm can be a mel filterbank feature extraction algorithm, an mfcc feature extraction algorithm and so on.

Step 103: identifying the passenger state according to the feature data of different dimensions.

Specifically, in this embodiment, all the feature data of different dimensions can be input into a total identification algorithm to identify the passenger state; alternatively, the feature data of each dimension may also be input into a corresponding identification algorithm, and passenger state probability data corresponding to the feature data of each dimension is output, then a weighted summation calculation is performed on the passenger state probability data of each dimension according to a preset weight of the passenger state probability data of each dimension, thus general passenger state probability data is obtained, and the final state of the passenger is determined according to the general passenger state probability data and a preset threshold.

It can be understood that, in this embodiment, the manner for identifying the passenger state according to the feature data of different dimensions may be other manner, which is not limited in this embodiment.

In this case, the identified passenger state may be a danger state or a safety state.

In the method for identifying the passenger state in the unmanned vehicle provided by this embodiment, monitoring data of different dimensions in a process where a passenger takes an unmanned vehicle is obtained; feature extraction is performed on the monitoring data of different dimensions and feature data of different dimensions is formed; and the passenger state is identified according to the feature data of different dimensions. By obtaining the monitoring data of various dimensions in the process where a passenger takes the unmanned vehicle to identify the passenger state, it is possible to omnidirectionally monitor the personal safety and property safety of the passengers, and effectively protect the passenger taking the unmanned vehicle.

Embodiment 2

Figure 2:
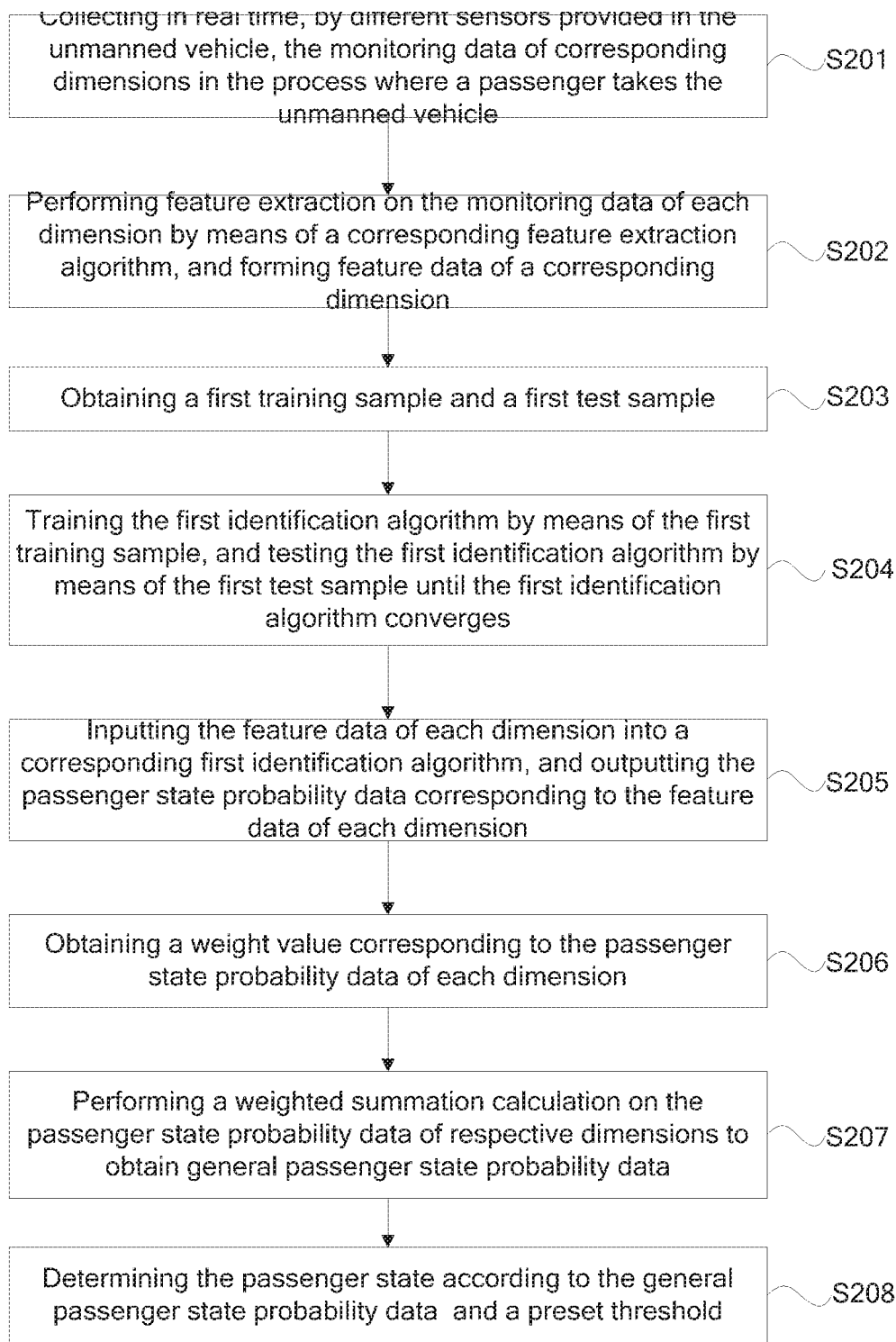
FIG. 2 is a flowchart of a method for identifying a passenger state in an unmanned vehicle according to Embodiment 2 of the present application.

FIG. 2 is a flowchart of a method for identifying a passenger state in an unmanned vehicle according to Embodiment 2 of the present application. As shown in FIG. 2, the method for identifying a passenger state in an unmanned vehicle according to this embodiment is based on the method for identifying the passenger state in the unmanned vehicle provided in Embodiment 1 of the present application, and further refines the steps 101 to 103. The method for identifying the passenger state in an unmanned vehicle provided by this embodiment includes the following steps.

Step 201, collecting in real time, by different sensors provided in the unmanned vehicle, the monitoring data of corresponding dimensions in the process where a passenger takes the unmanned vehicle.

Further, in this embodiment, the sensors include at least: an internal camera, a microphone, a vital sign sensor, and a collision sensor.

In this case, the internal camera is provided in the passenger seating area to capture a video or image of the passenger. The microphone can also be provided in the passenger seating area to collect the passenger's voice or other sounds. The vital sign sensor can be provided on the seat belt, and when taking the unmanned vehicle, the passenger wears the seat belt, or the passenger wears a device with a vital sign sensor to monitor the vital signs of the passenger. The collision sensor is provided on the inner side of the vehicle body or on the seat back of the passenger seat, and collects the collision data when the passenger collides with the inside of the vehicle body or the seat back.

Preferably, in this embodiment, collecting in real time, by different sensors provided in the unmanned vehicle, the monitoring data of the corresponding dimensions in the process where a passenger takes the unmanned vehicle specifically includes:

Firstly, collecting, by the internal camera, the expression monitoring data and the limb movement monitoring data in the process where the passenger takes the unmanned vehicle.

Further, in this embodiment, the number of internal cameras may be one or more. If there are multiple internal cameras, the internal cameras are provided in different directions of the passenger seating area. A video and an image of the passenger's face are captured by one or more internal cameras out of all the internal cameras, and the passenger's expression monitoring data is obtained from the video and the image of the face. And a video and an image of the passenger's whole body are captured by the rest one or more internal cameras, and limb movement monitoring data is obtained from the video and image of the whole body.

Secondly, collecting, by the microphone, the sound monitoring data in the process where the passenger takes the unmanned vehicle.

Further, in this embodiment, the number of the microphones may be one or more. If there are multiple microphones, the microphones are provided in different directions of the passenger seating area, and the voices of the passengers and other sounds in the unmanned vehicle are collected by the microphones to form the sound monitoring data.

Thirdly, collecting, by the vital sign sensor, vital sign monitoring data in the process where the passenger takes the unmanned vehicle.

Further, in this embodiment, the vital sign monitoring data collected by the vital sign sensor in the process where the passenger takes the unmanned vehicle may include: body temperature data, heartbeat data, blood pressure data, and the like.

Finally, collecting, by the collision sensor, the collision data of colliding the vehicle body or the seat in the process where a passenger takes the unmanned vehicle.

Further, in this embodiment, the collision sensors are installed on both the inner side of the vehicle body and the seat back, and the collision sensors collect the collision data when the passenger collides with the inner side of the vehicle body or the seat back.

It can be understood that each sensor can collect the monitoring data of the corresponding dimension in real time after the passenger gets on the vehicle and before getting off the vehicle.

It should be noted that, in this embodiment, step 201 is a further refinement of the step 101 of the method for identifying the passenger state in the unmanned vehicle provided in Embodiment 1 of the present application.

Step 202: performing feature extraction on the monitoring data of each dimension by means of a corresponding feature extraction algorithm, and forming feature data of a corresponding dimension.

In this embodiment, there is a corresponding feature extraction algorithm for the monitoring data of each dimension. For example, as for the expression monitoring data, the corresponding feature extraction algorithm may be a PCA feature extraction algorithm, an ICA feature extraction algorithm, and the like. For the sound monitoring data, the corresponding feature extraction algorithm may be a mel filterbank feature extraction algorithm, an mfcc feature extraction algorithm, and the like.

Further, in this embodiment, the expression feature extraction algorithm is used to perform feature extraction on the expression monitoring data to form expression feature data. The limb movement feature extraction algorithm is used to perform the feature extraction on the limb movement monitoring data to form the limb movement feature data. The sound feature extraction algorithm is used to perform the feature extraction on the sound monitoring data to form sound feature data. The vital sign feature extraction algorithm is used to perform the feature extraction on the vital sign monitoring data to form vital sign feature data. The collision feature extraction algorithm is used to perform the feature extraction on the collision data to form collision feature data.

Step 203: obtaining a first training sample and a first test sample.

In this case, the first training sample and the first test sample are feature data of the same dimension of each passenger. There are multiple first training samples and test samples.

Further, in this embodiment, before the feature data of each dimension is input into the corresponding first identification algorithm and the passenger state probability data corresponding to the feature data of each dimension is output, the first identification algorithm needs to be optimized to form an optimized first identification algorithm.

In this case, the first identification algorithm is an algorithm for determining passenger state probability data corresponding to the feature data of each dimension. The first identification algorithm is a deep learning algorithm, such as a convolutional neural network model algorithm, a deep neural network model algorithm, or the like.

In this embodiment, the first training sample and the first test sample are the training sample and the test sample corresponding to the first identification algorithm, where the first training sample and the first test sample may be feature data of the same dimension of each passenger that has occurred. As for the identification algorithm for identifying the passenger state probability based on the expression feature data, the training sample and the test sample are expression feature data of each passenger that has occurred. As another example, for an identification algorithm for identifying passenger state probability based on sound feature data, the training sample and test sample are sound feature data of each passenger that has occurred.

Step 204: training the first identification algorithm by means of the first training sample, and testing the first identification algorithm by means of the first test sample until the first identification algorithm converges.

Further, in this embodiment, each first training sample is input into the first identification algorithm; the model of the first identification algorithm is trained; the parameters are optimized; and each first test sample is input to the optimized first identification algorithm; then it is determined whether the model of the first identification algorithm is optimal, and if not, the training for the model of the first identification algorithm is continued until the model of the first identification algorithm converges to be optimal, It can be understood that after the first identification algorithm is the optimized identification algorithm, it is not necessary: to perform step 203-step 204 every time the passenger state is identified.

Step 205: inputting the feature data of each dimension into a corresponding first identification algorithm, and outputting the passenger state probability data corresponding to the feature data of each dimension.

In this embodiment, the feature data of each dimension is input into the corresponding first identification algorithm, where the first identification algorithm is a first identification algorithm optimized after a training and test process, and the first identification algorithm identifies the passenger state according to the feature data of the corresponding dimension, and the corresponding passenger state probability data is output.

In this case, the passenger state probability data is the probability data of the passenger danger state or the probability data of the passenger safety state, which is not limited in this embodiment.

Step 206: obtaining a weight value corresponding to the passenger state probability data of each dimension.

Further, in this embodiment, the weight value corresponding to the passenger state probability data of each dimension is predefined and stored, and the weight value corresponding to the passenger state probability data of each dimension is obtained from a storage area.

Step 207: performing a weighted summation calculation on the passenger state probability data of respective dimensions to obtain general passenger state probability data.

Further, in this embodiment, the passenger state probability data of each dimension is multiplied by the corresponding weight value, and the multiplied results are summed, then the obtained result is the general passenger state probability data. If the passenger state probability data of each dimension is the probability data of the passenger danger state, the general passenger state probability data is the general probability data of the passenger danger state. If the passenger state probability data of each dimension is probability data of the passenger safety state, the general passenger state probability data is the general probability data of the passenger safety state.

Step 208: determining the passenger state according to the general passenger state probability data and a preset threshold.

Further, in this embodiment, a danger probability threshold corresponding to the general probability of the passenger danger state and a safety probability threshold corresponding to the general probability of the passenger safety state are defined in advance.

In this case, the specific values of the danger probability threshold and the safety probability threshold are not limited in this embodiment.

If the value corresponding to the general probability data of the passenger danger state is greater than the preset danger probability threshold, then it is determined that the passenger state is a danger state; if the value corresponding to the general probability data of the passenger danger state is less than or equal to the preset danger probability threshold, it is determined that the passenger state is a safety state. Or if the value corresponding to the general probability data of the passenger safely state is greater than the preset safety probability threshold, it is determined that the passenger state is the safety state; if the value corresponding to general probability data of the passenger safety state is less than or equal to the preset safety probability threshold, it is determined that the passenger state is the danger state.

In the method for identifying the passenger state in the unmanned vehicle provided by this embodiment, the monitoring data of corresponding dimensions in the process where the passenger takes the unmanned vehicle is collected by different sensors provided in the unmanned vehicle in real time; and feature extraction is performed on the monitoring data of each dimension by means of a corresponding feature extraction algorithm, thus feature data of corresponding dimension is formed, feature data of each dimension is input into the corresponding first identification algorithm and the passenger state probability data corresponding to each dimension feature data is output, thus a weight value corresponding to the passenger state probability data of each dimension is obtained; a weighted summation calculation is performed on passenger state probability data of respective dimensions to obtain general passenger state probability data; determining the passenger state according to the general passenger state probability data and the preset threshold enables the omnidirectional monitoring on the personal safety and property safety of the passengers, further, the accuracy for identifying passenger state is effectively improved by using the optimized deep learning algorithm to identify the passenger state.

Embodiment 3

Figure 3:
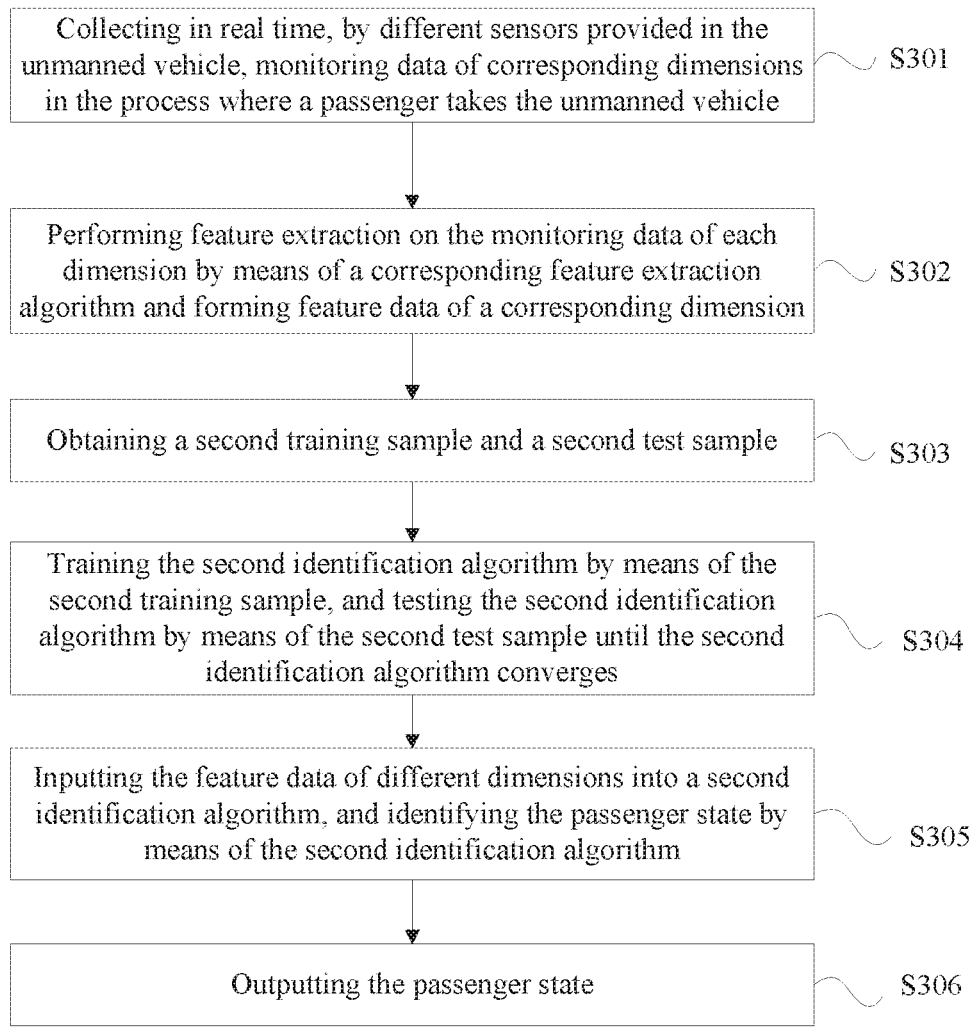
FIG. 3 is a flowchart of a method for identifying a passenger state in an unmanned vehicle according to Embodiment 3 of the present application.

FIG. 3 is a flowchart of a method for identifying a passenger state in an unmanned vehicle according to Embodiment 3 of the present application. As shown in FIG. 3, the method for identifying a passenger state in an unmanned vehicle according to this embodiment is based on the method for identifying the passenger state in the unmanned vehicle provided in Embodiment 1 of the present application, and further refines the steps 101 to 103. The method for identifying the passenger state in an unmanned vehicle provided by this embodiment includes the following steps.

Step 301: collecting in real time, by different sensors provided in the unmanned vehicle, monitoring data of corresponding dimensions in the process where a passenger takes the unmanned vehicle.

Step 302: performing feature extraction on the monitoring data of each dimension by means of a corresponding feature extraction algorithm and forming feature data of a corresponding dimension.

In this embodiment, the implementation of the steps 301-302 is the same as the implementation of the steps 201-202 in the method for identifying the passenger state in the unmanned vehicle provided in Embodiment 2 of the present application, and details are not described herein again.

Step 303: obtaining a second training sample and a second test sample.

In this case, the second training sample and the second test sample are feature data of different dimensions of each passenger.

Further, in this embodiment, before the feature data of different dimensions is input into a second identification algorithm and the passenger state is identified by the second identification algorithm, the second identification algorithm needs to be optimized to form an optimized second identification algorithm.

In this case, the second identification algorithm is an algorithm for identifying the passenger state through feature data of all dimensions. The second identification algorithm is a deep learning algorithm, such as a convolutional neural network model algorithm, a deep neural network model algorithm, or the like.

In this embodiment, the second training sample and the second test sample are the training sample and the test sample corresponding to the second identification algorithm, where the second training sample and the second test sample are feature data of all dimensions of each passenger that has occurred.

Step 304: training the second identification algorithm by means of the second training sample, and testing the second identification algorithm by means of the second test sample until the second identification algorithm converges.

Further, in this embodiment, each second training sample is input into the second identification algorithm, the model of the second identification algorithm is trained, the parameters are optimized; and each second test sample is input to the optimized second identification algorithm; then it is determined whether the model of the second identification algorithm is optimal, and if not, the training for the model of the second identification algorithm is continued until the model of the second identification algorithm converges to be optimal.

It can be understood that after the second identification algorithm is the optimized identification algorithm, it is not necessary to perform step 303-step 304 every time the passenger state is identified.

Step 305: inputting the feature data of different dimensions into a second identification algorithm, and identifying the passenger state by means of the second identification algorithm.

Step 306: outputting the passenger state.

Further, in this embodiment, the feature data of all dimensions of the monitored passenger is input into the second identification algorithm, and the second identification algorithm identifies the passenger state according to the feature data of all dimensions, and the passenger state is output. If the passenger state is identified as a danger state according to the feature data of all dimensions, the passenger danger state is output, and if the passenger state is identified as a safety state according to the feature data of all dimensions, the passenger safety state is output.

It can be understood that the identity information of the passenger and the contact information of the family are pre-stored in the unmanned vehicle. If the passenger state is the danger state, the passenger danger state, the identity information of the passenger and the contact information of the family are reported to the server through the communication module, such that the server notifies the passenger's family according to the identity information of the passenger and the contact information of the family. A GPS module may also be provided on the unmanned vehicle, through which the unmanned vehicle can be located, and the position of the unmanned vehicle may be sent to the server, so that the server obtains the position of the unmanned vehicle that the passenger takes, thus the passenger can be rescued in time.

In the method for identifying the passenger state in the unmanned vehicle provided by this embodiment, the monitoring data of the corresponding dimensions is collected in real time in the process where a passenger takes the unmanned vehicle by means of different sensors provided in the unmanned vehicle; feature extraction is performed on the monitoring data of each dimension by means of a corresponding feature extraction algorithm and feature data of the corresponding dimension is formed; a second training sample and a second test sample are obtained; the second identification algorithm is trained by means of the second training sample, and the second identification algorithm is tested by means of the second test sample until the second identification algorithm converges; the feature data of different dimensions is input into a second identification algorithm; and the passenger state is identified by the second identification algorithm, then the passenger state is output. The method enables the omnidirectional monitoring on the personal safety and property safety of the passengers, further the accuracy for identifying passenger state is effectively improved by using the optimized deep learning algorithm to identify the passenger state.

Embodiment 4

Figure 4:
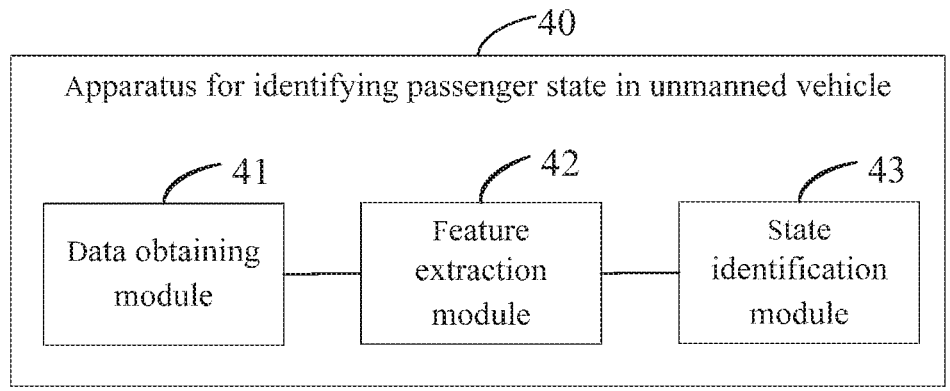
FIG. 4 is a schematic structural diagram of an apparatus for identifying a passenger state in an unmanned vehicle according to Embodiment 4 of the present application.

FIG. 4 is a schematic structural diagram of an apparatus for identifying a passenger state in an unmanned vehicle according to Embodiment 4 of the present disclosure. As shown in FIG. 4, the apparatus 40 for identifying a passenger state in an unmanned vehicle according to this embodiment includes: a data obtaining module 41, a feature extraction module 42 and a state identification module 43.

In this case, the data obtaining module 41 is configured to obtain monitoring data of different dimensions in the process where the passenger takes the unmanned vehicle. The feature extraction module 42 is configured to perform feature extraction on the monitoring data of different dimensions and form feature data of different dimensions. The state identification module 43 is configured to identify the passenger state according to the feature data of different dimensions.

The apparatus for identifying the state of the passenger in the unmanned vehicle provided in this embodiment can perform the technical solution of the method embodiment shown in FIG. 1, and the implementation principle and technical effects thereof are similar, thus details are not described herein again.

Embodiment 5

Figure 5:
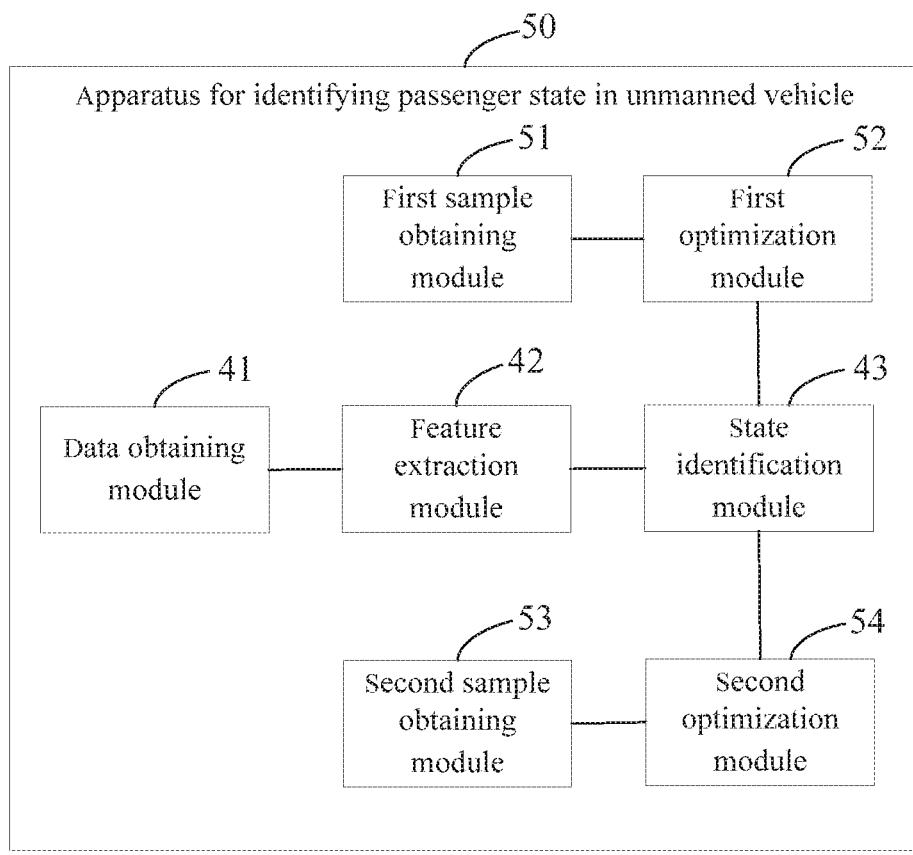
FIG. 5 is a schematic structural diagram of an apparatus for identifying a passenger state in an unmanned vehicle according to Embodiment 5 of the present application.

FIG. 5 is a schematic structural diagram of an apparatus for identifying a passenger state in an unmanned vehicle according to Embodiment 5 of the present disclosure. As shown in FIG. 5, based on the apparatus for identifying a passenger state in an unmanned vehicle provided in Embodiment 4 of the present application, the apparatus 50 for identifying a passenger state in an unmanned vehicle provided in this embodiment further includes: a first sample obtaining module 51, a first optimization module 52, a second sample obtaining module 53 and a second optimization module 54.

Further, the data obtaining module 41 is specifically configured to: collect real time, by means of different sensors provided in the unmanned vehicle, the monitoring data of the corresponding dimensions in the process where a passenger takes the unmanned vehicle.

Further, the sensors include at least: an internal camera, a microphone, a vital sign sensor, and a collision sensor.

Further, the data obtaining module 41 is specifically configured to: collect, by means of the internal camera, expression monitoring data and limb movement monitoring data in the process where the passenger takes the unmanned vehicle; and collect, by means of the microphone, sound monitoring data in the process where the passenger takes the unmanned vehicle; collect, by means of the vital signs sensor, the vital sign monitoring data in the process where the passenger takes the unmanned vehicle; collect, by means of the collision sensor, the collision data of colliding the vehicle body or the seat in the process where the passenger takes the unmanned vehicle.

Further, the feature extraction module 42 is specifically configured to: perform feature extraction on the monitoring data of each dimension by means of a corresponding feature extraction algorithm, and form feature data of the corresponding dimension.

Optionally, the state identification module 43 is specifically configured to: input the feature data of each dimension into the corresponding first identification algorithm, and output the passenger state probability data corresponding to the feature data of each dimension; obtain a weight value corresponding to the passenger state probability data of each dimension; perform a weighted summation calculation on passenger state probability data of respective dimensions to obtain general passenger state probability data; determine the passenger state according to the general passenger state probability data and a preset threshold.

Optionally, the state identification module 43 is specifically configured to: input the feature data of different dimensions into a second identification algorithm, and identify the passenger state by means of the second identification algorithm; output the passenger state.

Optionally, the first identification algorithm is a deep learning algorithm. The first sample obtaining module 51 is configured to obtain the first training sample and the first test sample, where the first training sample and the first test sample are feature data of the same dimension of each passenger. The first optimization module 52 is configured to train the first identification algorithm by means of the first training sample, and test the first identification algorithm by means of the first test sample until the first identification algorithm converges.

Optionally, the second identification algorithm is a deep teaming algorithm. The second sample obtaining module 53 is configured to obtain the second training sample and the second test sample, where the second training sample and the second test sample are feature data of different dimensions of each passenger. The second optimization module 54 is configured to train the second identification algorithm by means of the second training sample, and test the second identification algorithm by means of the second test sample until the second identification algorithm converges.

The apparatus for identifying the passenger state in the unmanned vehicle provided in this embodiment can perform the technical solution of the method embodiment shown in FIG. 2 or FIG. 3.As the implementation principle and technical effects are similar, details are not described herein again.

Embodiment 6

Figure 6:
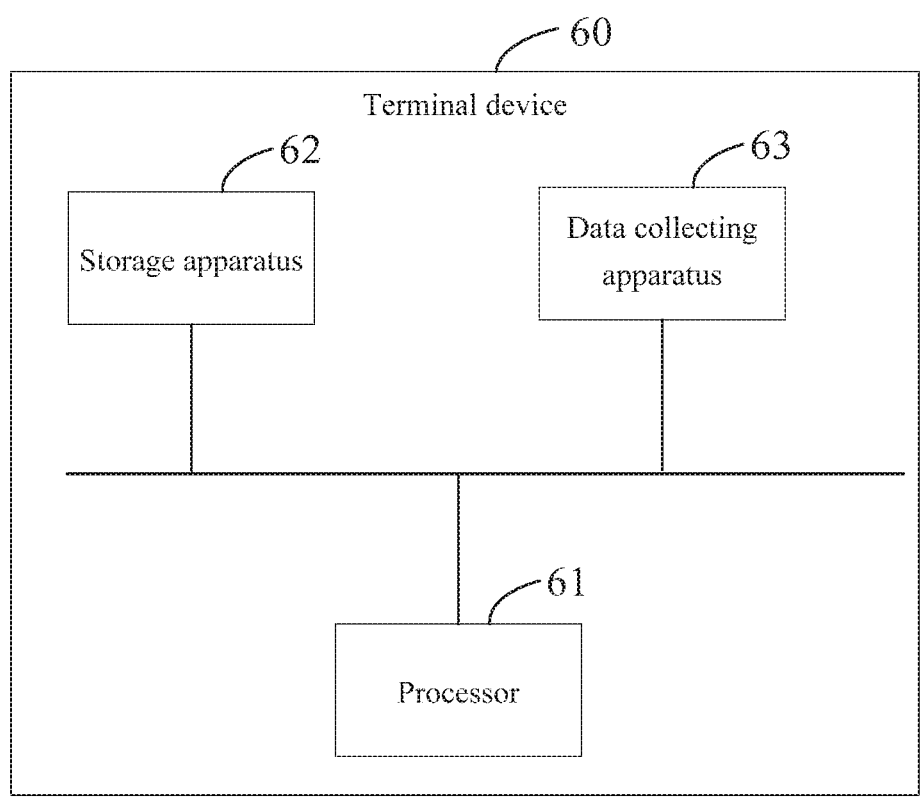
FIG. 6 is a schematic structural diagram of a terminal device according to Embodiment 6 of the present application.

FIG. 6 is a schematic structural diagram of a terminal device according to Embodiment 6 of the present application. As shown in FIG. 6, the terminal device 60 provided in this embodiment includes: one or more processors 61, a storage apparatus 62, and a data collecting apparatus 63.

The storage apparatus 62 is configured to store one or more programs. The data collecting apparatus 63 is configured to collect monitoring data of different dimensions. The one or more programs, when executed by one or more processors, cause the one or more processors to implement the method for identifying the passenger state in the unmanned vehicle provided in Embodiment 1 of the present application or the unmanned method for identifying the passenger state in the unmanned vehicle provided in Embodiment 2 of the present application or the method for identifying the passenger state in the unmanned vehicle provided in Embodiment 3 of the present application.

The related description can be understood by referring to the related descriptions and effects corresponding to the steps in FIG. 1 to FIG. 3, and no further description is made here.

Embodiment 7

Embodiment 7 of the present application provides a computer readable storage medium, on which a computer program is stored, and the computer program is executed by the processor to implement the method for identifying the passenger state in the unmanned vehicle provided in Embodiment 1 of the present application or the unmanned method for identifying the passenger state in the unmanned vehicle provided in Embodiment 2 of the present application or the method for identifying the passenger state in the unmanned vehicle provided in Embodiment 3 of the present application.

In the several embodiments provided by the present disclosure, it should be understood that the disclosed apparatus and method may be implemented in other manners. For example, the apparatus embodiments described above are merely illustrative. For example, the division of the modules is only a logical function division. In actual implementation, there may be another division manner, for example, multiple modules or components may be combined or integrated into another system, or some features may be ignored or not implemented. Alternatively, the coupling, direct coupling or communication connection shown or discussed may be an indirect coupling or communication connection through some interfaces, apparatuses or modules, and may be in electrical, mechanical or other form.

The modules described as separate components may or may not be physically separated, and the components illustrated as modules may or may not be physical modules, that is, the components may be located in one place, or may be distributed to multiple network modules. Some or all of the modules may be selected according to actual needs to achieve the objectives of the solution of the embodiment.

In addition, each functional module in each embodiment of the present application may be integrated into one processing module, or each unit may exist physically separately, or two or more modules may be integrated into one module. The above integrated module may be implemented in the form of hardware or in the form of a combination of hardware and software functional modules.

Program codes for implementing the method of the present application can be written in any combination of one or more programming languages. The program codes may be provided to a general purpose computer, a special purpose computer or a processor or controller of other programmable data processing apparatus such that the program codes, when executed by the processor or controller, cause the functions operations specified in the flowcharts and/or block diagrams to be implemented. The program codes may be executed entirely or partly on the machine, or be executed, as a stand-alone software package, partly on the machine and partly on the remote machine, or be executed entirely on a remote machine or a server.

In the context of the present application, a machine-readable medium may be a tangible medium that may include or store a program for use by or be used in connection with an instruction execution system, apparatus, or device. The machine readable medium can be a machine readable signal medium or a machine readable storage medium. A machine-readable medium can include, but is not limited to, electronic, magnetic, optical, electromagnetic, infrared, or semiconductor system apparatus or device, or any suitable combination of the above. More specific examples of the machine-readable storage medium may include electrical connections based on one or more wires, a portable computer disk, a hard disk, a random access memory (RAM), a read only memory (ROM), an erasable programmable read only memory (EPROM or flash memory), an optical fiber, a compact disk read only memory (CD-ROM), an optical storage device, a magnetic storage device, or any suitable combination of the foregoing.

In addition, although the operations are depicted in a particular order, it should be understood that such operations are performed in the particular order shown or in a sequential order, or that all illustrated operations should be performed to achieve the desired results. Multitasking and parallel processing may be advantageous in certain circumstances. Likewise, several specific implementation details are included in the above discussion, which however should not be construed as limiting the scope of the disclosure. Certain features that are described in the context of separate embodiments can also be implemented in combination in a single implementation. Conversely, various features that are described in the context of a single implementation can be implemented in a plurality of implementations, either individually or in any suitable sub-combination.

Although the subject matter has been described in language specific to structural features and/or methodological acts, it should be understood that the subject matter defined in the appended claims is not necessarily limited to the specific features or acts described above. Instead, the specific features and acts described above are merely exemplary forms of implementing the claims.

What is claimed is:

1. A method for identifying a passenger state in an unmanned vehicle, comprising:
    obtaining monitoring data of different dimensions in a process where a passenger takes the unmanned vehicle, wherein the monitoring data of different dimensions comprises expression monitoring data, limb movement monitoring data, sound monitoring data, vital sign monitoring data, and collision data of colliding a vehicle body or a seat;
    performing feature extraction on the monitoring data of different dimensions and forming feature data of different dimensions;
    identifying the passenger state according to the feature data of different dimensions, wherein the passenger state comprises a safety state and a danger state; and
    executing at least one step of:
    reporting the danger state, identity information of the passenger and contact information of the passenger's family to a server, if the passenger state is the danger state, for the server to notify the passenger's family according to the identity information of the passenger and the contact information of the passenger's family, wherein the identity information of the passenger and the contact information of the passenger's family are pre-stored in the unmanned vehicle; and
    reporting position of the unmanned vehicle to the server, if the passenger's state is the danger state, for the server to obtain the position of the unmanned vehicle that the passenger takes, wherein the unmanned vehicle is located by a GPS module provided on the unmanned vehicle,
    wherein the identifying the passenger state according to the feature data of different dimensions comprises:
    inputting feature data of each dimension into a corresponding first identification algorithm, and outputting passenger state probability data corresponding to the feature data of each dimension;
    obtaining a weight value corresponding to the passenger state probability data of each dimension;
    performing a weighted summation calculation on passenger state probability data of respective dimensions to obtain general passenger state probability data; and
    determining the passenger state according to the general passenger state probability data and a preset threshold.

2. The method according to claim 1, wherein the obtaining monitoring data of different dimensions in a process where the passenger takes the unmanned vehicle comprises:
    collecting in real time, by different sensors provided in the unmanned vehicle, monitoring data of corresponding dimensions in the process where the passenger takes the unmanned vehicle.

3. The method according to claim 2, wherein the sensors comprise at least: an internal camera, a microphone, a vital sign sensor, and a collision sensor.

4. The method according to claim 3, wherein the collecting in real time, by different sensors provided in the unmanned vehicle, monitoring data of corresponding dimensions in the process where the passenger takes the unmanned vehicle, comprises:
    collecting, by the internal camera, the expression monitoring data and the limb movement monitoring data in the process where the passenger takes the unmanned vehicle;
    collecting, by the microphone, the sound monitoring data in the process where the passenger takes the unmanned vehicle;
    collecting, by the vital sign sensor, the vital sign monitoring data in the process where the passenger takes the unmanned vehicle; and
    collecting, by the collision sensor, the collision data of colliding a vehicle body or a seat in the process where the passenger takes the unmanned vehicle.

5. The method according to claim 1, wherein the performing feature extraction on the monitoring data of different dimensions and forming feature data of different dimensions comprises:
performing the feature extraction on the monitoring data of each dimension by means of a corresponding feature extraction algorithm and forming feature data of a corresponding dimension.

6. An apparatus for identifying a passenger state in an unmanned vehicle, comprising:
a processor and a computer-readable medium for storing program codes, which, when executed by the processor, cause the processor to: obtain monitoring data of different dimensions in a process where a passenger takes the unmanned vehicle, wherein the monitoring data of different dimensions comprises expression monitoring data, limb movement monitoring data, sound monitoring data, vital sign monitoring data, and collision data of colliding a vehicle body or a seat;
perform feature extraction on the monitoring data of different dimensions and form feature data of different dimensions;
identify the passenger state according to the feature data of different dimensions, wherein the passenger state comprises a safety state and a danger state; and
execute at least one step of:
reporting the danger state, identity information of the passenger and contact information of the passenger's family to a server, if the passenger state is the danger state, for the server to notify the passenger's family according to the identity information of the passenger and the contact information of the passenger's family, wherein the identity information of the passenger and the contact information of the passenger's family are pre-stored in the unmanned vehicle; and
reporting position of the unmanned vehicle to the server, if the passenger's state is the danger state, for the server to obtain the position of the unmanned vehicle that the passenger takes, wherein the unmanned vehicle is located by a GPS module provided on the unmanned vehicle,
wherein the program codes further cause the processor to:
input feature data of each dimension into a corresponding first identification algorithm, and output passenger state probability data corresponding to the feature data of each dimension;
obtain a weight value corresponding to the passenger state probability data of each dimension;
perform a weighted summation calculation on passenger state probability data of respective dimensions to obtain general passenger state probability data; and
determine the passenger state according to the general passenger state probability data and a preset threshold.

7. The apparatus according to claim 6, wherein the program codes further cause the processor to:
collect in real time, by different sensors provided in the unmanned vehicle, monitoring data of corresponding dimensions in the process where the passenger takes the unmanned vehicle.

8. The apparatus according to claim 7, wherein the sensors comprise at least:
an internal camera, a microphone, a vital sign sensor, a collision sensor.

9. The apparatus according to claim 8, wherein the program codes further cause the processor to:

collect, by the internal camera, the expression monitoring data and the limb movement monitoring data in the process where the passenger takes the unmanned vehicle;
collect, by the microphone, the sound monitoring data in the process where the passenger takes the unmanned vehicle;
collect, by the vital sign sensor, the vital sign monitoring data in the process where the passenger takes the unmanned vehicle; and
collect, by the collision sensor, the collision data of colliding a vehicle body or a seat in the process where the passenger takes the unmanned vehicle.

10. The apparatus according to claim 6, wherein the program codes further cause the processor to:
perform the feature extraction on the monitoring data of each dimension by means of a corresponding feature extraction algorithm and form feature data of a corresponding dimension.

11. A terminal device, comprising:
one or more processors;
wherein one or more programs, when executed by the one or more processors, cause the one or more processors to implement the method according to claim 1.

12. A non-transitory computer readable storage medium, having stored thereon a computer program, wherein the program is executed by a processor to implement the steps of:
obtaining monitoring data of different dimensions in a process where a passenger takes the unmanned vehicle, wherein the monitoring data of different dimensions comprises expression monitoring data, limb movement monitoring data, sound monitoring data, vital sign monitoring data, and collision data of colliding a vehicle body or a seat;
performing feature extraction on the monitoring data of different dimensions and forming feature data of different dimensions;
identifying the passenger state according to the feature data of different dimensions, wherein the passenger state comprises a safety state and a danger state; and
executing at least one step of:
reporting the danger state, identity information of the passenger and contact information of the passenger's family to a server, if the passenger state is the danger state, for the server to notify the passenger's family according to the identity information of the passenger and the contact information of the passenger's family, wherein the identity information of the passenger and the contact information of the passenger's family are pre-stored in the unmanned vehicle; and
reporting position of the unmanned vehicle to the server, if the passenger's state is the danger state, for the server to obtain the position of the unmanned vehicle that the passenger takes, wherein the unmanned vehicle is located by a GPS module provided on the unmanned vehicle,
wherein the identifying the passenger state according to the feature data of different dimensions comprises:
inputting feature data of each dimension into a corresponding first identification algorithm, and outputting passenger state probability data corresponding to the feature data of each dimension;
obtaining a weight value corresponding to the passenger state probability data of each dimension;

performing a weighted summation calculation on passenger state probability data of respective dimensions to obtain general passenger state probability data; and determining the passenger state according to the general passenger state probability data and a preset threshold.

* * * * *